(12) United States Patent
Sekiguchi et al.

(10) Patent No.: US 8,071,126 B2
(45) Date of Patent: Dec. 6, 2011

(54) PERCUTANEOUS ABSORPTION TYPE PATCH

(75) Inventors: Toru Sekiguchi, Higashimurayama (JP); Kaname Nakahara, Saitama (JP); Toru Watanabe, Kunitachi (JP)

(73) Assignee: LINTEC Corporation, Tokyo (JP)

( * ) Notice: Subject to any disclaimer, the term of this patent is extended or adjusted under 35 U.S.C. 154(b) by 205 days.

(21) Appl. No.: 12/666,435

(22) PCT Filed: Mar. 19, 2008

(86) PCT No.: PCT/JP2008/055108
§ 371 (c)(1),
(2), (4) Date: Dec. 23, 2009

(87) PCT Pub. No.: WO2009/001591
PCT Pub. Date: Dec. 31, 2008

(65) Prior Publication Data
US 2010/0189751 A1    Jul. 29, 2010

(30) Foreign Application Priority Data
Jun. 26, 2007   (JP) ................. 2007-167294

(51) Int. Cl.
*A61F 13/00* (2006.01)
*A61F 13/02* (2006.01)
*A61F 15/00* (2006.01)
*B23B 9/00* (2006.01)

(52) U.S. Cl. .......... 424/449; 424/448; 428/42.3; 602/57

(58) Field of Classification Search .................. None
See application file for complete search history.

(56) References Cited

U.S. PATENT DOCUMENTS
4,627,429 A    12/1986  Tsuk
4,917,929 A *  4/1990  Heinecke ................ 428/41.4
(Continued)

FOREIGN PATENT DOCUMENTS
JP        60-54284       11/1985
(Continued)

OTHER PUBLICATIONS

Extended European Search Report for European Application No. 08722483.8, dated Apr. 29, 2011, 6 pages.

(Continued)

*Primary Examiner* — Robert A Wax
*Assistant Examiner* — Olga V Tcherkasskaya
(74) *Attorney, Agent, or Firm* — Brinks Hofer Gilson & Lione

(57) ABSTRACT

A percutaneous absorption type patch adapted to be applied to a skin surface of a patient. The percutaneous absorption type patch comprises: a stratum-corneum release member constituted from a sheet-like first supporting substrate and a pressure-sensitive adhesive layer laminated on the first supporting member; a medicinal-components administration member constituted from a sheet-like second supporting substrate, a medicinal-components retention layer laminated on the second supporting substrate, and a protect layer laminated on the medicinal-components retention layer; and a sheet-like handling member interposed between the stratum-corneum release member and the medicinal-components administration member. An edge portion of the handling member is coupled to or integrated with both the first supporting substrate and the protect layer. Operations of peeling the stratum-corneum release member from the skin surface of the patient and peeling the protect layer from the medicinal-components retention layer are carried out at a time by pulling the handling member toward an operating direction.

4 Claims, 2 Drawing Sheets

U.S. PATENT DOCUMENTS

| | | | | |
|---|---|---|---|---|
| 4,928,680 | A | * | 5/1990 | Sandbank ............ 602/57 |
| 6,124,522 | A | * | 9/2000 | Schroeder ............ 602/57 |
| 6,129,929 | A | * | 10/2000 | Wick ............ 424/448 |
| 6,140,548 | A | * | 10/2000 | Hansen et al. ............ 602/57 |
| 6,140,549 | A | * | 10/2000 | Pompei, Jr. ............ 602/57 |
| 6,573,421 | B1 | * | 6/2003 | Lemaire ............ 602/57 |
| 7,027,877 | B2 | * | 4/2006 | Dupelle et al. ............ 607/142 |
| 2005/0034732 | A1 | | 2/2005 | Rousseau et al. |
| 2006/0051403 | A1 | | 3/2006 | Matriano et al. |
| 2006/0074376 | A1 | | 4/2006 | Kwon |
| 2006/0233871 | A1 | | 10/2006 | Stern et al. |

FOREIGN PATENT DOCUMENTS

| | | |
|---|---|---|
| JP | 63-9546 | 3/1988 |
| JP | 2005-200391 A | 7/2005 |
| WO | WO 2005/042054 A2 | 5/2005 |

OTHER PUBLICATIONS

International Search Report for International Application No. PCT/JP2008/055108, dated May 1, 2008, 2 pages.

Seo, N. et al., Proceedings of the National Academy of Sciences of the USA, vol. 97, p. 371-376, 2000.

* cited by examiner

PERCUTANEOUS ABSORPTION TYPE PATCH

FIELD OF THE INVENTION

The present invention relates to a percutaneous absorption type patch.

In medical treatments using medicinal components such as immunization for preventing virus diseases such as flu, measles, and the like, an injection device is generally used to administrate the medicinal component into a patient (a living body), but the use of such an injection device gives considerable pain to the patient.

As a method of administrating such medicinal components to patients without giving such pain, there is know a method of applying a percutaneous absorption type patch preparation to the skin of a patient. However, there is a case that the skin of a patient has old stratum corneum. In such a case, only by simply applying the percutaneous absorption type patch preparation to the skin, it is difficult to allow the medicinal components to penetrate into the skin due to the presence of the old stratum corneum. In particular, in a case where a biological preparation such as a vaccine, a chemical preparation containing compounds having a high molecular weight, and the like are used as the medicinal components, it is extremely difficult to allow the medicinal components to be percutaneously adsorbed.

In order to solve such a problem, a new methods is proposed (e.g., two documents described below), in which an old stratum corneum of the skin of a patient is removed in advance using an adhesive or a pressure-sensitive adhesive sheet before a percutaneous absorption type preparation is applied to the skin.

However, in the above method, the percutaneous absorption type preparation is applied to the same part as a part of the skin of the patient from which the old stratum corneum has been removed. Therefore, the part needs to be marked by writing instruments and the like, which may give the patient discomfort feeling. Further, in a case where a patient carries out the above method by himself, it is difficult to apply a percutaneous absorption type preparation to his loin or back. Furthermore, wrinkles are likely to occur to the percutaneous absorption type preparation when it is applied to the skin of the loin or back. As a result, there is a problem in that it is not possible to sufficiently administrate the medicinal components into the patient.

The two documents are JP-A 2005-200391 and Seo N et al., Proc Natl Acad Sci USA, 97:371-376, 2000 as examples of related art.

SUMMARY OF THE INVENTION

It is therefore an object of the present invention to provide a percutaneous absorption type patch which is capable of removing old stratum corneum of a skin surface of a patient and applying a medicinal-components administration member to the skin surface of the patient body with sequential operation.

In order to achieve the above object, the present invention is directed to a percutaneous absorption type patch adapted to be applied to a skin surface of a patient. The percutaneous absorption type patch comprises: a stratum-corneum release member constituted from a sheet-like first supporting substrate and a pressure-sensitive adhesive layer laminated on the first supporting member, and the pressure-sensitive adhesive layer having a function of removing an old stratum corneum from the skin surface of the patient; a medicinal-components administration member constituted from a sheet-like second supporting substrate, a medicinal-components retention layer laminated on the second supporting substrate, and a protect layer laminated on the medicinal-components retention layer, wherein the medicinal-components retention layer includes medicinal components, the protect layer has a function of protecting the medicinal-components retention layer, and the protect layer is capable of peeling from the medicinal-components retention layer; and a sheet-like handling member interposed between the stratum-corneum release member and the medicinal-components administration member, the handling member being adapted to be operated to an operating direction, and the handling member having an edge portion at a side thereof which is opposite to the operating direction. The edge portion of the handling member is coupled to or integrated with both the first supporting substrate and the protect layer. Operations of peeling the stratum-corneum release member from the skin surface of the patient and peeling the protect layer from the medicinal-components retention layer are carried out at a time by pulling the handling member toward the operating direction.

According to the present invention, it is possible to provide a percutaneous absorption type patch which is capable of removing old stratum corneum of a skin surface of a patient and applying a medicinal-components administration member to the skin surface of the patient with an easy and sequential operation.

In the percutaneous absorption type patch according to the present invention, it is preferred that the handling member is constituted from two layers including a first layer and a second layer laminated on the first layer. The first layer is integrally formed with the first supporting substrate, and the second layer is integrally formed with the protect layer.

In the percutaneous absorption type patch according to the present invention, it is also preferred that the medicinal-components retention layer has a part not to be covered with the protect layer, and the part is provided so as to extend from a position corresponding to the edge portion of the handling member toward the opposite direction of the operating direction.

In the percutaneous absorption type patch according to the present invention, it is also preferred that the medicinal components include biological preparation.

DESCRIPTION OF EXEMPLARY EMBODIMENTS

Hereinbelow, a percutaneous absorption type patch according to the present invention will be described in detail based on preferred embodiments thereof.

Figure 1:
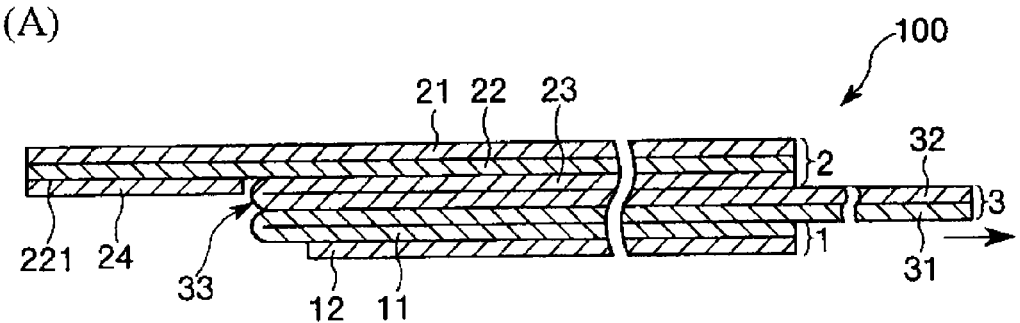
FIGS. 1 (A) and (B) are cross-sectional views showing a preferred embodiment of a percutaneous absorption type patch according to the present invention.
Figure 1:
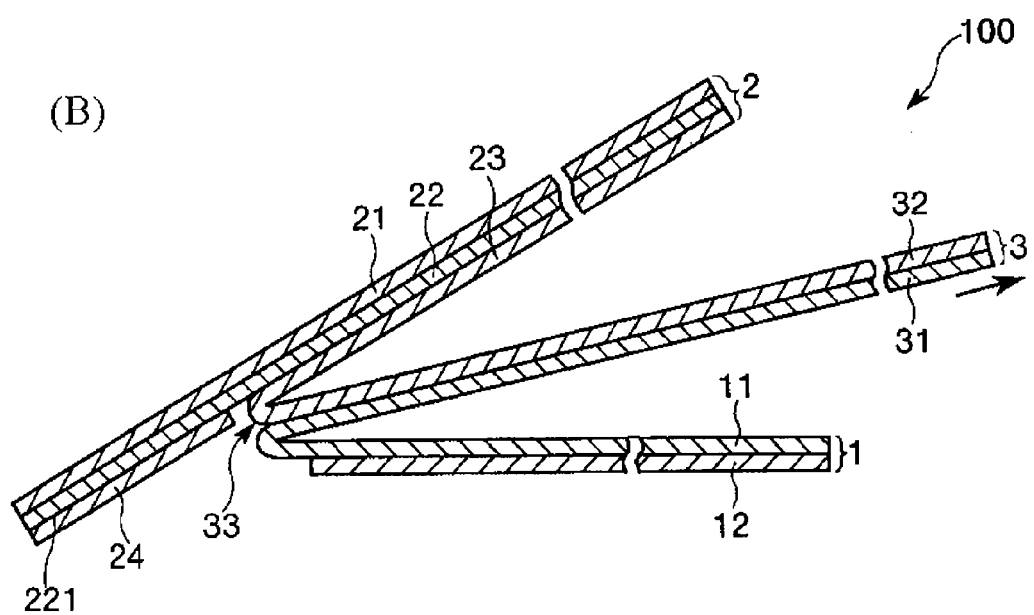

FIGS. 1 (A) and (B) are cross-sectional views showing a preferred embodiment of a percutaneous absorption type patch according to the present invention. FIG. 1 (A) is the cross-sectional view showing a usual status of the preferred embodiment of the percutaneous absorption type patch according to the present invention. FIG. 1 (B) is the cross-sectional view showing a spreading status of the preferred embodiment of the percutaneous absorption type patch according to the present invention. In the following description, the upper side in FIG. 1 (A) will be referred to as "upper", the lower side thereof will be referred to as "lower", the right side thereof will be referred to as "right" or "operating direction", and the left side thereof will be referred to as "left" for convenience of explanation.

As shown in FIGS. 1 (A) and (B), a percutaneous absorption type patch 100 is constituted from a stratum-corneum release member 1, a medicinal-components administration member 2, and an handling member 3.

Further, as shown in FIG. 1 (A), the percutaneous absorption type patch 100 is formed by laminating the stratum-corneum release member 1, the handling member 3, and the medicinal-components administration member 2 in this order from the lower of the drawing.

As shown in FIGS. 1 (A) and (B), the stratum-corneum release member 1 is constituted form a first supporting substrate 11 and a pressure-sensitive adhesive layer 12 formed (laminated) on a lower surface of the first supporting substrate 11.

The first supporting substrate 11 is a member formed in a sheet form, and has a function of supporting the pressure-sensitive adhesive layer 12. Such a first supporting substrate 11 has flexibility (plasticity) and curve following capability when applying the percutaneous absorption type patch 100. Further, it is preferred that the first supporting substrate 11 is suitable for cutting, punching, or the like during a processing treatment.

The first supporting substrate 11 is constituted from, for example, a plastic film such as a polyester film (e.g., a polyethylene terephthalate film, or the like), a polyolefin film (e.g., a polyethylene film, a polypropylene film, an ethylene-methacrylic acid copolymer film, an ethylene-methyl methacrylate copolymer film, or the like), a polyurethane film, a thermoplastic elastomer resin (e.g., polystyrene, or the like), or the like; a fabric, a knitted fabric, and an nonwoven fabric, which are formed of various kinds of synthetic fibers and/or natural fibers; paper such as glassine paper, woodfree paper, coated paper, or the like; or laminated body formed by these materials.

An average thickness of the first supporting substrate 11 is preferably in the range of 10 to 800 μm, and more preferably in the range of 20 to 500 μm.

The pressure-sensitive adhesive layer 12 has a function of removing old stratum corneum from the skin surface of the patient by applying it to the skin surface of the patient and releasing it.

A pressure-sensitive adhesive constituting the pressure-sensitive adhesive layer 12 is not limited to a specific material as long as the old stratum corneum is capable of being removed from the skin surface of the patient due to adhesion (adhesive force) thereof. Examples of such a pressure-sensitive adhesive include a rubber-based pressure-sensitive adhesive, an acrylic pressure-sensitive adhesive, a silicone-based pressure-sensitive adhesive, and the like. Among the pressure-sensitive adhesives, the acrylic pressure-sensitive adhesive is preferable in view of the adhesion that the old stratum corneum is reliably removed from the skin surface of the patient, irritant property to the skin, and the like. Further, in the acrylic pressure-sensitive adhesive, it is more preferred that (metha) acrylic polymer (a) having crosslinkable functional groups, (metha) acrylic oligomer (b) having lactam rings, and a crosslinking agent (c) are contained therein. A pressure-sensitive adhesive composition for releasing stratum corneum which are disclosed in JP-A 2007-289672 and JP-A 2007-038273 can preferably be used as such a pressure-sensitive adhesive.

An adhesion of the pressure-sensitive adhesive layer 12 is preferably in the range of 2 to 20 N/25 mm, and more preferably in the range of 3 to 12 N/25 mm. Such an adhesion is measured at five minutes after the pressure-sensitive adhesive layer 12 is bonded to a bakelite according to JIS Z0237 (mode: 180° releasing, releasing speed: 300 mm/min, adhering period: 5 minutes). If the adhesion of the pressure-sensitive adhesive layer 12 is smaller than the above lower limit value, there is a case that the old stratum corneum cannot be sufficiently removed from the skin surface of the patient. On the other hand, if the adhesion of the pressure-sensitive adhesive layer 12 exceeds the above upper limit value, there is a case that patients feel a pain when the pressure-sensitive adhesive layer 12 is released (removed) from the skin surface of the patient. Further, there is another case that the pressure-sensitive adhesive constituting the pressure-sensitive adhesive layer 12 remains on the skin surface of the patient.

An average thickness of the pressure-sensitive adhesive layer 12 is preferably in the range of 15 to 100 μm, and more preferably in the range of 25 to 50 μm.

Before the percutaneous absorption type patch 100 is used, a release sheet (not shown) is applied to the surface of the pressure-sensitive adhesive layer 12. When the percutaneous absorption type patch 100 is used, the release sheet is removed (released) from the surface of the pressure-sensitive adhesive layer 12.

As shown in FIG. 1 (A), the medicinal-components administration member 2 is provided above the upper surface of the stratum-corneum release member 1 through the handling member 3 (side of the stratum-corneum release member 1 in which the first support substrate 11 is provided). The medicinal-components administration member 2 is constituted from a second supporting substrate 21, a medicinal-components retention layer 22, and a protect layer 23.

As shown in FIG. 1 (A), the medicinal-components administration member 2 is formed by laminating the second support substrate 21, the medicinal-components retention layer 22, and the protect layer 23 in this order from the upper of the drawing.

The second supporting substrate 21 is a member formed in a sheet form, and has a function of supporting the medicinal-components retention layer 22. Such a second supporting substrate 21 has flexibility (plasticity) and curve following capability when applying the percutaneous absorption type patch 100. Additionally, it is preferred that the second supporting substrate 21 is suitable for cutting, punching, or the like during a processing treatment.

The second supporting substrate 21 is constituted of the same materials as that of the first supporting substrate 11 described above.

An average thickness of the second supporting substrate 21 is preferably in the range of 10 to 800 μm, and more preferably in the range of 20 to 500 μm.

The medicinal-components retention layer 22 is laminated (formed) on the side of the stratum-corneum release member 1 of the second supporting substrate 21 as shown in FIG. 1 (A).

The medicinal-components retention layer 22 has adherence (adhesion) and is capable of adhering to the skin surface of the patient. Such a medicinal-components retention layer 22 includes medicinal-components (properties).

The medicinal-components retention layer 22 has a function of being capable of administrating (slowly-releasing) the medicinal components into the patient when the percutaneous absorption type patch 100 is applied to the skin surface of the patient.

The medicinal-components retention layer 22 can be provided (exhibited) adherence by including the pressure-sensitive adhesive as described above therein.

A type (composition) of the medicinal-components retention layer 22 is not limited to a specific type as long as the medicinal components are retained and the retained medicinal components are slowly-released in the patient. Examples of the type of the medicinal-components retention layer 22 include a reservoir type, a matrix type, and the like. The reservoir type is a type which has a medicinal-components reservoir and a pressure-sensitive adhesive layer to apply to a skin. The matrix type is a type that medicinal components are included in polymers of a pressure-sensitive adhesive.

Examples of the medicinal components included in such a medicinal-components retention layer 22 include: a synthetic formulation such as an analgesic antiphlogistic agent which includes indomethacin, ketoprofen, flurbiprofen, diclofenac, loxoprofen, ketorolac, felbinac (4-biphenyl acetic acid) and the like; various kinds of vitamin such as vitamin C, vitamin E and the like; biological preparation such as vaccine which includes influenza vaccine and hepatitis virus vaccine, an antibiotic which includes a beta-lactam derivative antibiotic and an amidoglycoside derivative antibiotic, and the like.

Among the medicinal components, generally, most of the biological preparations produce a relatively strong side-effects. Such biological preparations are administrated into the patient by the percutaneous absorption in order to lessen and inhibit the side-effects. However, in a conventional percutaneous absorption type preparation, medicinal components could not sufficiently be administrated due to low percutaneous absorption property thereof. In contrast, by using the percutaneous absorption type patch 100 according to the present invention, it is possible to reliably remove the old stratum corneum from the skin surface of the patient. Further, the medicinal-components administration member 2 (medicinal-components retention layer 22) can be applied to the skin surface of the patient with an easy method without crinkles and the like which are likely to occur when applying the medicinal-components retention layer 22 thereto. Therefore, it is possible to reliably use the percutaneous absorption type patch 100 for administrating the biological preparation into the patient.

In a case where the percutaneous absorption property of the medicinal components is low, the medicinal-components retention layer 22 may be provided with a microneedle. This makes it possible to improve the percutaneous absorption property of the medicinal components.

An average thickness of the medicinal-components retention layer 22 is preferably in the range of 10 to 3000 µm, and more preferably in the range of 20 to 1000 µm.

The protect layer 23 has a function of protecting the medicinal-components retention layer 22 and is capable of peeling from the medicinal-components retention layer 22.

Examples of a constituent material of the protect layer 23 include: paper such as glassine paper, coated paper, cast coated paper, or the like; a polyester film such as a polyethylene terephthalate film, a polybuthylene terephthalate film, polyethylene naphtalate film, or the like; a polyolefin film such as a polypropylene film, a polyethylene film, or the like. A release agent such as a silicone resin may be applied to the surface of the protect layer 23.

An average thickness of the protect layer 23 is preferably in the range of 20 to 500 µm, and more preferably in the range of 25 to 150 µm.

In this embodiment, an area of the surface of the medicinal-components retention layer 22 when the medicinal-components retention layer 22 is planar-viewed is larger than an area of the surface of the protect layer 23 when the protect layer is planar-viewed. As shown in FIG. 1 (A), the medicinal-components retention layer 22 is lengthened to a left direction than the protect layer 23 and has a part 221 not to be covered with the protect layer 23. In other words, the medicinal-components retention layer 22 is lengthened toward an opposite direction with respect to an operating direction of the handling member 3 (an arrow direction in FIG. 1 (A)) than an edge portion 33 of the handling member 3 described later, and has the part 221 not to be covered with the protect layer 23. In the use of the percutaneous absorption type patch 100, it is possible for such a part 221 to be used as a positioning means of the medicinal-components administration member 2 by applying the part 221 to the skin surface of the patient before the handling member 3 described later is operated. This makes it possible to prevent crinkles and the like from occurring and apply the medicinal-components administration member 2 (medicinal-components retention layer 22) to the skin surface of the patient with an easy operation.

As shown in FIG. 1 (A), the part 221 not to be covered with the protect layer 23 is applied to a release sheet 24 before the percutaneous absorption type patch 100 is used. When the percutaneous absorption type patch 100 is used, the release sheet 24 is peeled off.

Constituent materials of the release sheet 24 and a release sheet to be formed on the pressure-sensitive adhesive layer 12 which is not shown in FIG. 1 (A) can be the same material as that of the protect layer 23 described above.

The handling member 3 is a member formed in a sheet form. As shown in FIG. 1 (A), the handling member 3 is interposed between the stratum-corneum release member 1 and the medicinal-components administration member 2. The handling member 3 is handled (operated) by pulling it in a direction of the arrow shown in FIG. 1 (A).

As shown in FIG. 1 (A), the handling member 3 is formed by laminating a second layer 32 and a first layer 31 provided on the stratum-corneum release member 1 in this order. Further, the first layer 31 and the second layer 32 are firmly bonded by an adhesive, a pressure-sensitive adhesive, a heat-sealing means, or the like.

As shown in FIG. 1 (A), the first layer 31 is integrated with the first supporting substrate 11 of the stratum-corneum release member 1 described above at the edge portion 33 of the first layer 31 which is positioned in the opposite direction with respect to the operating direction (pulling direction) of the handling member 3. In other words, the first layer 31 is integrally formed with the first supporting substrate 11. Further in other words, the first layer 31 and the first supporting substrate 11 are formed by folding one film at a predetermined position thereof.

As shown in FIG. 1 (A), the second layer 32 is integrated with the protect layer 23 of the medicinal-components administration member 2 described above at the edge portion 33 of the second layer 32 which is positioned in the opposite direction with respect to the operating direction of the handling member 3. In other words, the second layer 32 is integrally formed with the protect layer 23. Further in other words, second layer 32 and the protect layer 23 are formed by folding one film at a predetermined position thereof.

The handling member 3 is formed by integrating with the first supporting substrate 11 and the protect layer 23 at the edge portion 33. Therefore, if the handling member 3 is pull to the arrow direction in FIG. 1 (A) in a state that the pressure-sensitive adhesive layer 12 of the stratum-corneum release member 1 is applied to the skin surface of the patient, it is possible to accomplish the following two peelings at a time. The one peeling is that the pressure-sensitive adhesive layer 12 of the stratum-corneum release member 1 is peeled from the skin surface of the patient. The other peeling is that the protect layer 23 is peeled from the medicinal-components retention layer 22. This makes it possible to prevent occurrence of crinkles and the like. Further, it is also possible to apply the medicinal-components administration member 2 to the skin surface of the patient with the easy operation.

An average thickness of the handling member 3 is preferably in the range of 30 to 1300 μm, and more preferably in the range of 45 to 650 μm.

The above description has been made on that the handling member 3 is formed by integrating with the first supporting substrate 11 and the protect layer 23 at the edge portion 33. However, these formations are not limited thereto. For example, a constituent material of the handling member 3 may be different from those of the first supporting substrate 11 and the protect layer 23, and the handling member 3 may be physically connected (coupled) with the first supporting substrate 11 and the protect layer 23.

Further, the above description has been made on that handling member 3 is constituted from two layers, namely the first layer 31 and the second layer 32. However, the handling member 3 may be constituted from one layer or three or more layers.

Furthermore, the length of the handling member 3 in the operating direction is preferably larger than the length of each of the protect layer 23 and the stratum-corneum release member 1 in the operation direction. This makes it possible to handpick an edge portion of the handling member 3 to thereby handle (operate) it.

Next, a description will be made on a method of using the percutaneous absorption type patch 100 described above.

Figure 2:
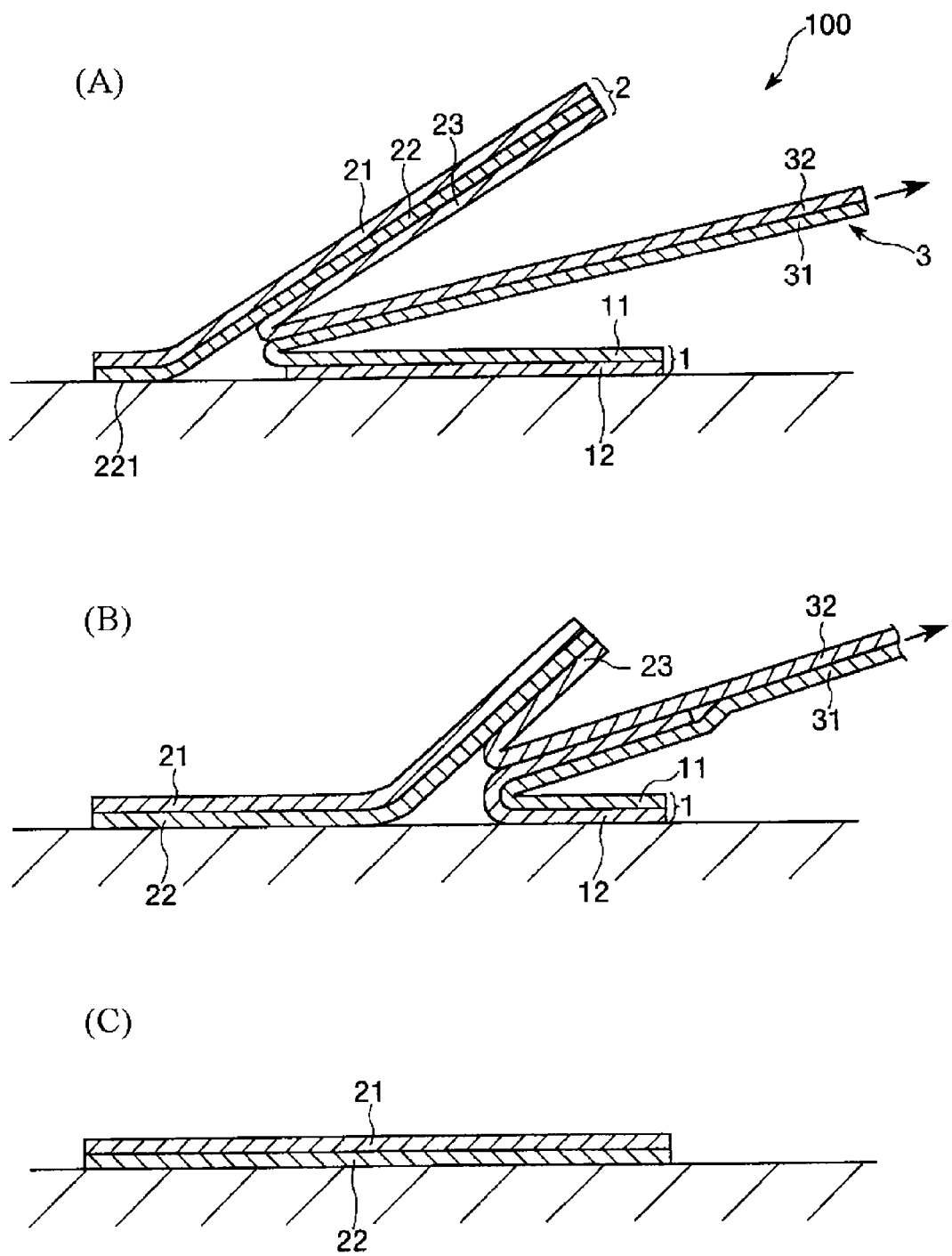
FIGS. 2 (A) to (C) are perspective views for explaining a method of using a percutaneous absorption type patch according to the present invention.

FIG. 2 is a perspective view for explaining a method of using a percutaneous absorption type patch 100 according to the present invention.

First, a release sheet, which is not shown in drawings, is removed from the pressure-sensitive adhesive layer 12. Further, the release sheet 24 is also removed from the medicinal-components retention layer 22.

Next, as shown in FIG. 2 (A), the pressure-sensitive adhesive layer 12 is applied to the skin surface of the patient. Further, the part 221 of the medicinal-components retention layer 22 is also applied to the skin surface of the patient.

Then, in such a state, the handling member 3 is pull to the arrow direction in FIGS. 2 (A) and (B). This makes it possible to peel the pressure-sensitive adhesive layer 12 of the stratum-corneum release member 1 from the skin surface of the patient and the protect layer 23 from the medicinal-components retention layer 22 as shown in FIG. 2 (B). As a result, the medicinal-components administration member 2 is gradually applied to the skin surface of the patient.

Thereafter, the handling member 3 is further pull to the arrow direction in FIG. 2 (B). In this way, the stratum-corneum release member 1 is entirely peeled from the skin surface of the patient as shown in FIG. 2 (C). Finally, the medicinal-components administration member 2 is applied to the skin surface of the patient.

As described above, by using the percutaneous absorption type patch according to the present invention, it is possible to remove the old stratum corneum from the skin surface of the patient and apply the medicinal-components administration member to the skin surface of the patient with the easy sequential operation. Further, it is also possible to easily apply the medicinal-components administration member to parts such as loin and back to which it is difficult to apply in one hand.

The description has been made on the percutaneous absorption type patch according to the present invention. However, the present invention is not limited thereto.

INDUSTRIAL APPLICABILITY

According to the present invention, it is possible to be capable of removing old stratum corneum of a skin surface of a patient and applying a medicinal-components administration member to the skin surface of the patient body with an easy and sequential operation. Accordingly, the present invention has industrial applicability.

What is claimed is:

1. A percutaneous absorption type patch adapted to be applied to a skin surface of a patient, comprising:
    a stratum-corneum release member constituted from a sheet-like first supporting substrate and a pressure-sensitive adhesive layer laminated on the first supporting member, and the pressure-sensitive adhesive layer having a function of removing an old stratum corneum from the skin surface of the patient;
    a medicinal-components administration member constituted from a sheet-like second supporting substrate, a medicinal-components retention layer laminated on the second supporting substrate, and a protect layer laminated on the medicinal-components retention layer, wherein the medicinal-components retention layer includes medicinal components, the protect layer has a function of protecting the medicinal-components retention layer, and the protect layer is capable of peeling from the medicinal-components retention layer; and
    a sheet-like handling member interposed the stratum-corneum release member and the medicinal-components administration member, the handling member being adapted to be operated to an operating direction, and the handling member having an edge portion at a side thereof which is opposite to the operating direction;
    wherein the edge portion of the handling member is coupled to or integrated with both the first supporting substrate and the protect layer, and
    wherein operations of peeling the stratum-corneum release member from the skin surface of the patient and peeling the protect layer from the medicinal-components retention layer are carried out at a time by pulling the handling member toward the operating direction.

2. The percutaneous absorption type patch as claimed in claim 1, wherein the handling member is constituted from two layers including a first layer and a second layer laminated on the first layer,
    wherein the first layer is integrally formed with the first supporting substrate, and the second layer is integrally formed with the protect layer.

3. The percutaneous absorption type patch as claimed in claim 1, wherein the medicinal-components retention layer has a part not to be covered with the protect layer, and the part is provided so as to extend from a position corresponding to the edge portion of the handling member toward the opposite direction of the operating direction.

4. The percutaneous absorption type patch as claimed in claim 1, wherein the medicinal components include biological preparation.

* * * * *